(12) United States Patent
Tokunaga et al.

(10) Patent No.: US 6,881,322 B2
(45) Date of Patent: Apr. 19, 2005

(54) MEASURING DEVICE USING BIOSENSOR AND BIOSENOR USED FOR IT, AND DEDICATED STANDARD LIQUID

(75) Inventors: Hiroyuki Tokunaga, Ehime (JP); Shoji Miyazaki, Ehime (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 456 days.

(21) Appl. No.: 09/937,300

(22) PCT Filed: Jan. 25, 2001

(86) PCT No.: PCT/JP01/00471
§ 371 (c)(1),
(2), (4) Date: Dec. 6, 2001

(87) PCT Pub. No.: WO01/55712
PCT Pub. Date: Aug. 2, 2001

(65) Prior Publication Data
US 2002/0179440 A1 Dec. 5, 2002

(30) Foreign Application Priority Data
Jan. 25, 2000 (JP) ........................... 2000-015320

(51) Int. Cl.[7] ............................................ G01N 27/327
(52) U.S. Cl. ................... 205/775; 205/777.5; 204/400; 204/403.14; 204/403.01
(58) Field of Search .............................. 204/400, 403.16, 204/403.01–403.14

(56) References Cited

U.S. PATENT DOCUMENTS 5,264,103 A    11/1993   Yoshioka et al. .......... 205/778
5,395,504 A *   3/1995   Saurer et al. .......... 204/403.03
5,650,062 A     7/1997   Ikeda et al. .............. 205/778

FOREIGN PATENT DOCUMENTS

| EP | 0732406 | 9/1996 | ............ C12Q/1/00 |
| EP | 735363 | 10/1996 | ......... G01N/27/327 |

OTHER PUBLICATIONS

Patent Abstracts of Japan, vol. 013, No. 169 (C–587), Apr. 21, 1989 & JP 63 317097 A (Matsushita Electric In Co Ltd), Dec. 26, 1988.
Patent Abstracts of Japan, vol. 014, No. 245 (P–1052), May 24, 1990 & JP 02 062952 A (Matsushita Electric Ind Co Ltd). Mar. 2, 1990.
Patent Abstracts of Japan, vol. 013, No. 382 (P–923), Aug. 24, 1989 & JP 01 134246 A (Matsushita Electric Ind Co Ltd), May 26, 1989.
Patent Abstracts of Japan, vol. 012, No. 399 (P–775), Oct. 24, 1988 & JP 63 139245 A (Matsushita Electric Ind Co Ltd). Jun. 11, 1988.

* cited by examiner

*Primary Examiner*—Alex Noguerola
(74) *Attorney, Agent, or Firm*—Wenderoth, Lind & Ponack, L.L.P.

(57) ABSTRACT

A reaction layer 12 which reacts with a substance to be measured in a sample solution is provided on a working electrode 1, a counter electrode 2, and a third electrode 3 which are provided on an insulating substrate 7 so as to bridge the respective electrodes, the content of the substance to be measured is measured from a current value which reaction is obtained between the working electrode 1 and the counter electrode 2, and the types of sample solution is judged by a difference between oxidation current values or between oxidation current waveforms, which are obtained between the third electrode 3 and the counter electrode 2 or between the third electrode 3 and the working electrode 1, thereby automatically judging the types of sample solution.

11 Claims, 3 Drawing Sheets

MEASURING DEVICE USING BIOSENSOR AND BIOSENOR USED FOR IT, AND DEDICATED STANDARD LIQUID

TECHNICAL FIELD

The present invention relates to a measuring apparatus using an electrode type of biosensor, a biosensor used therefor, and an exclusive standard solution.

BACKGROUND ART

In recent years, for example, a small-sized simple glucose level measuring apparatus using an electrode type of biosensor has been used to diagnose a glucose level of diabetics and has been used in daily management. FIG. 4 is an exploded perspective view illustrating an example of a structure of a glucose sensor, and silver leads 4 and 5 are formed by a screen printing or the like on an insulating substrate 7 of PET (Polyethylene Terephthalate).

A quadrangular working electrode 1 is formed by carbon on the tip of the silver lead 4, and a counter electrode 2 is formed so as to have a predetermined gap between the silver lead 5 and the working electrode 1 on the tip of the silver lead 5 and surround the working electrode 1. Terminal parts 4a and 5a connected to a measuring device at the measurement are formed on the other ends of the silver leads 4 and 5, respectively. On both electrodes 1 and 2 so formed, a reaction layer 12 comprising a CMC (Carboxyl Methyl Cellulose) layer which is a hydrophilic polymer, GOD (Glucose Oxidase) as an enzyme, and potassium ferricyanide as a mediator is formed so as to bridge and cover both of the electrodes 1 and 2.

Further, a cover 8 on the tip of which a sample supplying groove 10 having an opening 9 is formed over the layer 12 is attached on the substrate 7 such that an end part of the sample supplying groove 10 is located on the reaction layer 12, and an air hole 11 is formed on an end part of the sample supplying groove 10.

When the sensor so constructed is mounted on the small-sized simple measuring apparatus for measuring glucose level and then blood sample to be measured comes in contact with the opening 9 of the sample supplying groove 10, a fixed quantity (approximately 3 $\mu$L) of the sample is introduced into the reaction layer 12 by capillary action via the sample supplying groove 10, whereby predetermined reaction occurs. A current value accompanying the reaction is read on the measuring apparatus side through the terminal parts 4a and 5a, and the content of glucose as a substance to be measured is measured from the current value.

In the small-sized simple measuring apparatus as described above, recently, the emphasis has been, more particularly, on the field of data management such as the management and'processing of the measurement data, and, for example, the apparatus is constructed such that the measuring apparatus successively stores a measured value and can easily ascertain variations per hour, an average value or the like. Further, when accurate data management is made, it is required to maintain and manage the accuracy of the biosensor and the measuring apparatus. Therefore, the apparatus regularly measures using an exclusive glucose standard solution, thereby performing accuracy management thereof.

When the accuracy of the measuring apparatus is maintained and managed, a specified manual operation is performed on the measuring apparatus beforehand so as not to confuse the measurement data for accuracy management using the exclusive glucose standard solution with the measurement data using blood normally used as a sample, and switching is performed to a standard solution measurement mode when the measurement is made by the standard solution, where the apparatus is devised so as to discriminate between the blood measurement data and the exclusive glucose standard solution measurement data or the like.

However, when a manual preoperation is necessary in the measuring apparatus, data is managed in a state where the standard solution measurement data is incorrectly recognized as the blood measurement data due to an artificial incorrect operation, a forgotten operation or the like. More particularly, it is difficult for users having trouble with their eyes and fingers to perform the preoperation as described above, and therefore, a system which can automatically judge types of sample solution without operations has been desired.

The present invention is made to solve the above-described problems and has, for its object, to provide a measuring apparatus which can automatically judge types of sample solution without artificial operations, a biosensor used therefor, and an exclusive standard solution.

DISCLOSURE OF THE INVENTION

According to a first aspect of the present invention, in a measuring apparatus using a biosensor, which has a reaction layer which reacts with a substance to be measured in a sample solution, on a working electrode, a counter electrode, and a third electrode provided on an insulating substrate, so as to bridge the respective electrodes, the content of the substance to be measured is measured from a current value which is produced by a reaction between the substance to be measured and the reaction layer, which reaction is obtained between the working electrode and the counter electrode, and the types of sample solution are judged on the basis of an oxidation current value obtained between the third electrode and the counter electrode or between the third electrode and the working electrode.

Thereby, after introducing the sample solution, the types of sample solution can be automatically judged on the basis of an oxidation current value obtained between the third electrode and the counter electrode or between the third electrode and the working electrode, and the types of the sample solution can be automatically judged without artificial preoperation.

According to a second aspect of the present invention, in the measuring apparatus using the biosensor of the first aspect, judgment between the types of sample solution based on the oxidation current value is made by comparing an oxidation current value obtained between the third electrode and the counter-electrode or between the third electrode and the working electrode to a predetermined fixed threshold value.

Thereby, after introducing the sample solution, the types of sample solution can be automatically judged on the basis of an oxidation current value obtained between the third electrode and the counter electrode or between the third electrode and the working electrode, and the types of the sample solution can be automatically judged without artificial preoperation.

According to a third aspect of the present invention, in the measuring apparatus using the biosensor of the first aspect, judgment between the types of sample solution based on the oxidation current value is made on the basis of the time variations of the oxidation current value obtained between the third electrode and the counter electrode or between the third electrode and the working electrode.

Thereby, after introducing the sample solution, the types of sample solution can be automatically judged on the basis of an oxidation current value obtained between the third electrode and the counter electrode or between the third electrode and the working electrode, and the types of the sample solution can be automatically judged without artificial preoperation.

According to a fourth aspect of the present invention, in the measuring apparatus using the biosensor of the first aspect, the oxidation current value used for the judgment is the one which is measured at the point of time when a fixed time has further elapsed after the current value reaches a predetermined current value, which current flows between the third electrode and the counter electrode or between the third electrode and the working electrode.

Thereby, after introducing the sample solution, the types of sample solution can be automatically judged with higher accuracy on the basis of an oxidation current value obtained between the third electrode and the counter electrode or between the third electrode and the working electrode, and the types of the sample solution can be automatically judged without artificial preoperation.

According to a fifth aspect of the present invention, a biosensor comprises: a reaction layer which reacts with a substance to be measured in a sample solution so as to bridge the respective electrodes on a working electrode, a counter electrode, and a third electrode provided on an insulting substrate; and a connection terminal which is electrically connected to the working electrode, the counter electrode and the third electrode, respectively, on the insulating substrate.

Thereby, after introducing the sample solution into the biosensor, an oxidation current value obtained between the third electrode and the counter electrode or between the third electrode and the working electrode can be measured by the measuring apparatus using the biosensor, and the types of the sample solution can be automatically judged without artificial preoperation.

According to a sixth aspect of the present invention, in the biosensor of the fifth aspect, the third electrode consists of easily oxidized materials as compared with the working electrode and the counter electrode.

Thereby, the oxidation current value obtained between the third electrode and the counter electrode or between the third electrode and the working electrode and its variation characters are significantly different in accordance with whether or not organic acid is included in the sample solution introduced into the biosensor. Therefore, the types of the sample solution can be automatically judged by the measuring apparatus using the biosensor without artificial preoperation.

According to a seventh aspect of the present invention, in the biosensor of the fifth aspect, materials of the third electrode are the ones having lower dissolution potential than a voltage applied to the biosensor.

Thereby, after introducing the sample solution into the biosensor, an oxidation current value obtained between the third electrode and the counter electrode or between the third electrode and the working electrode can be measured by the measuring apparatus using the biosensor, and the types of the sample solution can be automatically judged without artificial preoperation.

According to an eighth aspect of the present invention, in the biosensor of the seventh aspect, materials of the third electrode are silver, copper, zinc, or mixed materials including silver, copper, and zinc.

Thereby, after introducing the sample solution into the biosensor, an oxidation current value obtained between the third electrode and the counter electrode or between the third electrode and the working electrode can be measured by the measuring apparatus using the biosensor, and the types of the sample solution can be automatically judged without artificial preoperation.

According to a ninth aspect of the present invention, in a biosensor's exclusive standard solution used for a measuring apparatus using a biosensor, which apparatus measures the content of the substance to be measured from a current value which is produced by a reaction between the substance to be measured and the reaction layer, which reaction is obtained between the working electrode and the counter electrode, and judges types of sample solution on the basis of an oxidation current value obtained between the third electrode and the counter electrode or between the third electrode and the working electrode, by using a biosensor providing a reaction layer which reacts with a substance to be measured in a sample solution so as to bridge the respective electrodes on a working electrode, a counter electrode, and a third electrode provided on an insulting substrate, a substance which suppresses oxidation current obtained by an oxidation of the third electrode is merged.

Thereby, an oxidation current value which is produced from the third electrode when this exclusive standard solution is introduced, and an oxidation current value which is produced from the third electrode when blood is measured are significantly different. Therefore, the types of the sample solution can be automatically judged by utilizing the above-described measuring apparatus using the biosensor without artificial preoperation.

According to a tenth aspect of the present invention, in the biosensor's exclusive standard solution of the ninth aspect, a substance which suppresses oxidation current obtained by an oxidation of the third electrode is organic acid.

Thereby, an oxidation current value which is produced from the third electrode when this exclusive standard solution is introduced, and an oxidation current value which is produced from the third electrode when blood is measured are significantly different. Therefore, the types of the sample solution can be automatically judged by utilizing the above-described measuring apparatus using the biosensor without artificial preoperation.

According to an eleventh aspect of the present invention, in the biosensor's exclusive standard solution of the tenth aspect, the organic acid is at least one of benzoic acid, citric acid, salicylic acid, sorbic acid, dehydroacetic acid, propionic acid.

Thereby, an oxidation current value which is produced from the third electrode when this exclusive standard solution is introduced, and an oxidation current value which is produced from the third electrode when blood is measured are significantly different. Therefore, the types of the sample solution can be automatically judged by utilizing the above-described measuring apparatus using the biosensor without artificial preoperation.

BEST MODE FOR CARRYING OUT THE INVENTION

Embodiment

Figure 1:
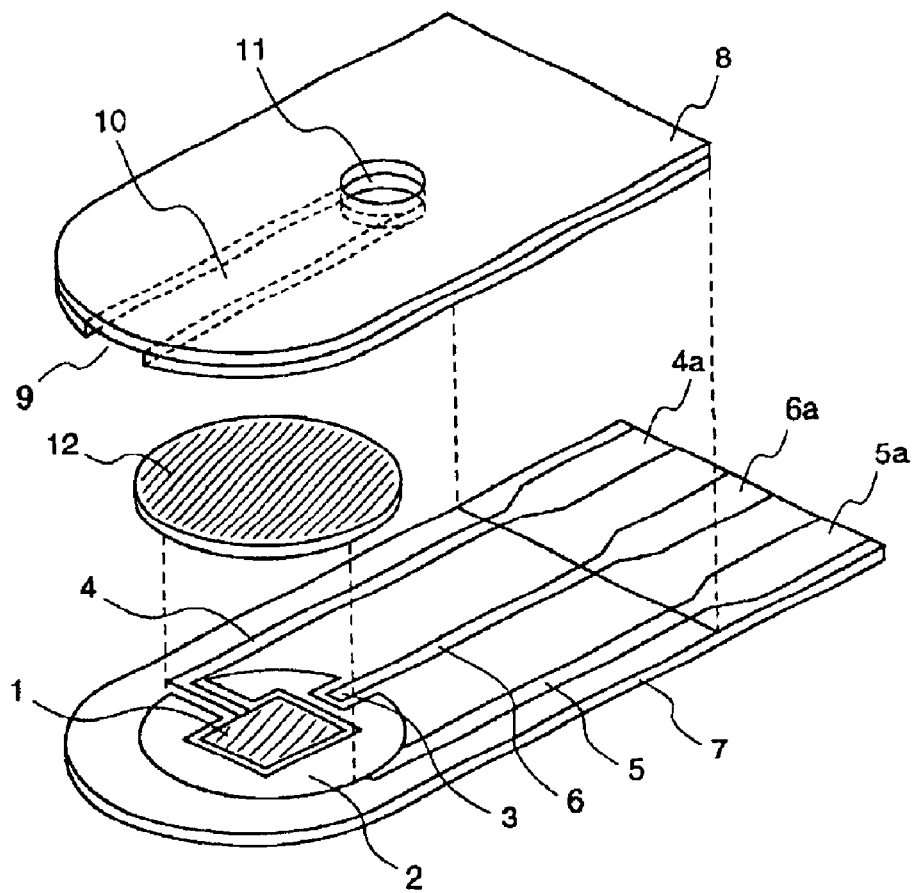
FIG. 1 is an exploded perspective view of a glucose sensor according to an embodiment of the present invention.
Figure 4:
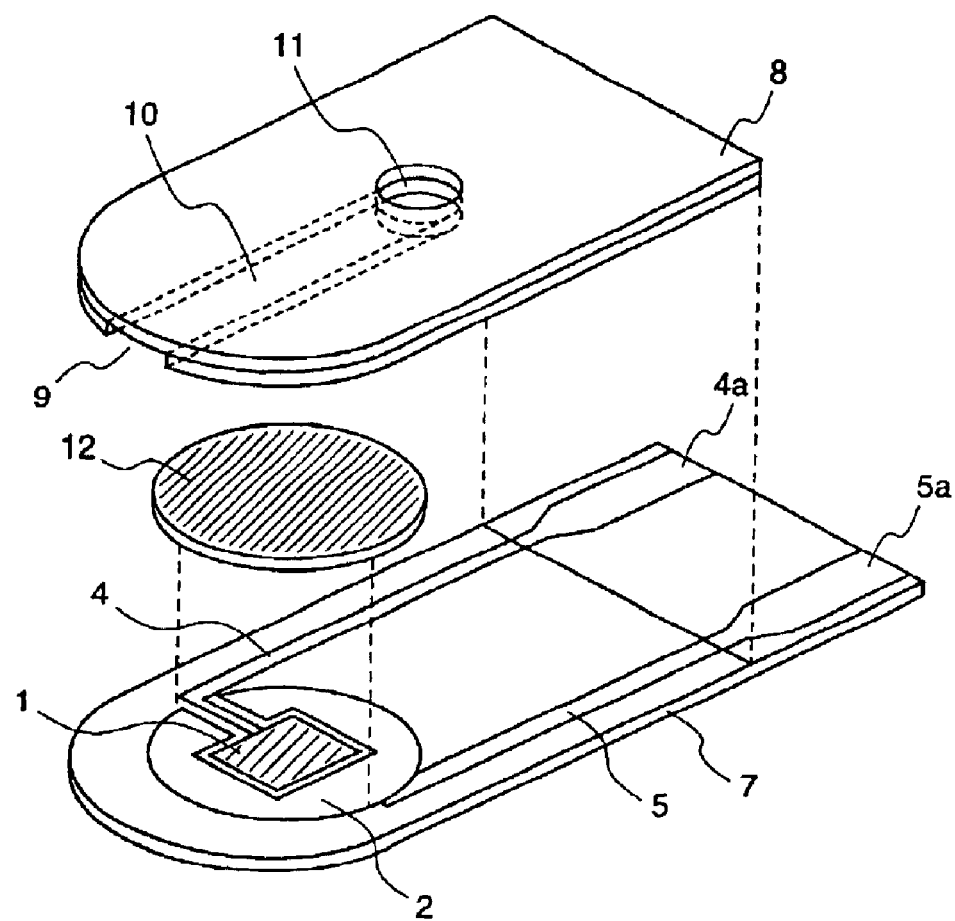
FIG. 4 is an exploded perspective view of a conventional glucose sensor.

FIG. 1 is an exploded perspective view illustrating a structure of a glucose sensor according to an embodiment of the present invention. The same numerals are given to the similar components as those of the conventional sensor shown in FIG. 4.

In FIG. 1, a point that the sensor is different from the conventional sensor is that a silver lead 6 is further provided besides silver leads 4 and 5. On the tip of the silver lead 6, a third electrode 3 for judging types of sample solution is arranged on an air hole 11 side in the vicinity of the working electrode 1 and the counter electrode 2, and, on the other end, a connection terminal part 6a is further formed. Further, on the working electrode 1, the counter electrode 2, and the third electrode 3, the reaction layer 12 is formed so as to bridge and cover the working electrode 1, the counter electrode 2, and the third electrode 3. Further, as long as this third electrode 3 is arranged in a position where the third electrode 3 comes in contact with the measurement sample, it may be arranged in any position.

Further, the third electrode 3 consists of easily oxidized materials as compared with the working electrode 1 and the counter electrode 2, and, for example, silver, copper, zinc, or mixed materials including them correspond to the easily oxidized materials. In this embodiment, a silver electrode is employed as the third electrode 3.

When the sensor so constructed comes in contact with the opening 9 of the sample supplying groove 10, a fixed quantity (here, as approximately 3 $\mu$L) of the sample is introduced into the reaction layer 12 and the respective electrode parts 1, 2 and 3 by capillary action, whereby suction of the samples reaches the third electrode 3 and then stops.

Figure 2:
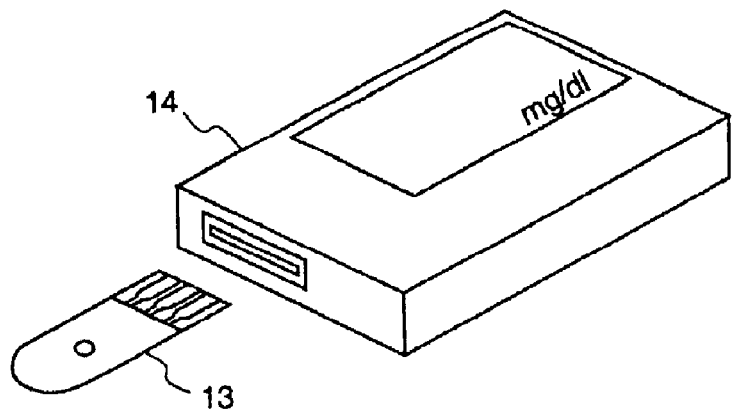
FIG. 2 is a perspective view of a glucose measuring device according to the embodiment of the present invention.

On the other hand, in contrast with the sensor, as a measuring device, one which is shown in FIG. 2 is employed. When a sensor 13 is mounted, the power to a measuring device 14 is turned on, and the measuring device is in a stand-by condition where a voltage of 0.5V is applied between the working electrode 1 and the third electrode 3 or between the counter 2 and the third electrode 3. This applied voltage values are different in accordance with the materials of the third electrode 3.

When a sample is introduced into the sensor 13 during the stand-by condition of the measuring device 14, a fixed quantity (here, as approximately 3 $\mu$L) of the sample is introduced into the reaction layer 12 and the respective electrode parts by capillary action via the sample supplying groove 10. Thereafter, when oxidation current which is measured in the third electrode 3 is the fixed quantity (here, as 0.3 $\mu$A/0.5 second) or more, an application of the voltage to the sensor 13 is once stopped, and the reaction proceeds for a predetermined time.

After the predetermined time has elapsed, the voltage is applied again, and the current value corresponding to glucose level is measured. The measurement of the current value corresponding to this glucose level is made, specifically, by applying a voltage of 0.5V between the working electrode 1 and the counter electrode 2 or among the working electrode 1, the counter electrode 2, and the third electrode 3, and measuring the current value obtained in the working electrode 1 at that time.

Next, the exclusive standard solution used for the measuring device 14 using the glucose sensor according to the present invention will be described.

The exclusive standard solution is characterized by further merging a substance which suppresses oxidation current with a conventional standard solution containing a fixed quantity of glucose. As substances which suppress the oxidation current, any organic acid is possible, and, for example, benzoic acid, citric acid, salicylic acid, sorbic acid, dehydroacetic acid, propionic acid, and the like are listed. In this embodiment, what is obtained by merging 0.1 weight % benzoic acid with the exclusive standard solution is employed. Further, the similar action is obtained when the addition amount of benzoic acid is 0.01 weight % or more.

Next, a method for automatically judging types of sample solution by using the glucose sensor according to the present invention will be described.

Initially, the voltage of 0.5V is applied to the third electrode 3 shown in FIG. 1, using the counter electrode 2 as reference, and stand-by is performed until the measurement sample is introduced. Further, while a description is given of a case where the voltage of 0.5V is applied to the third electrode 3, using the counter electrode 2 as reference, the voltage of 0.5V may be applied to the third electrode 3, using the working electrode 1 as reference.

Next, the measurement sample is introduced from the opening 9 of the sample supplying groove 10, and, when the sample reaches the third electrode 3, oxidation current is produced in the third electrode 3.

Figure 3:
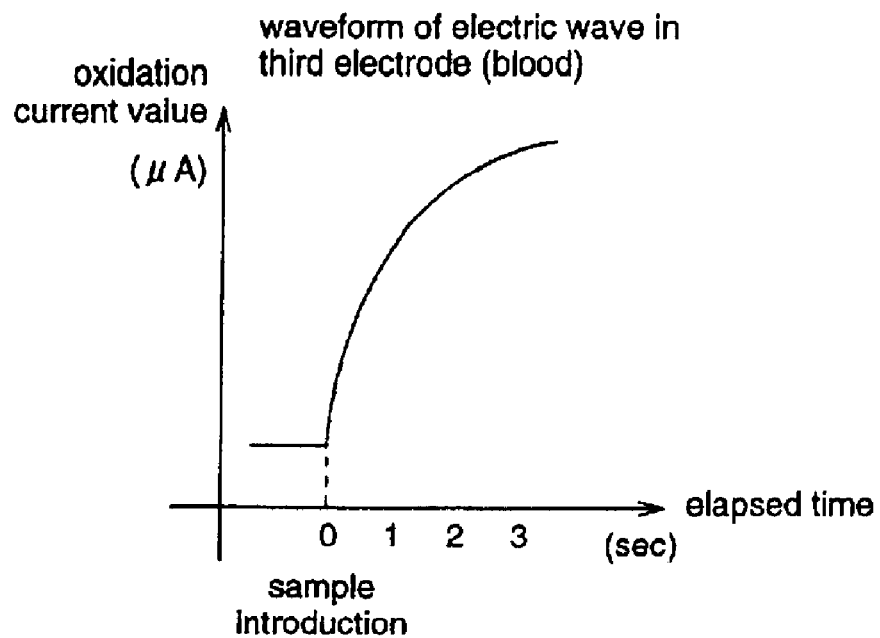
FIGS. 3(a) and 3(b) are diagrams illustrating oxidation current waveforms according to the embodiment of the present invention.
Figure 3:
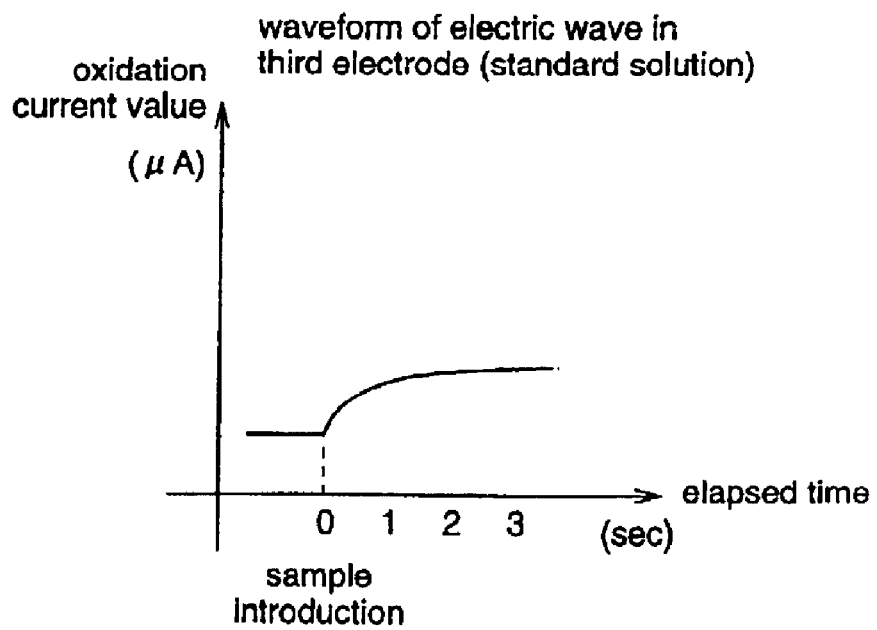

FIGS. 3(a) and 3(b) illustrate oxidation current values obtained by the third electrode 3 after introducing the measurement sample. FIG. 3(a) illustrates the oxidation current values at normal blood measurement, and FIG. 3(b) illustrates the oxidation current values at exclusive standard solution measurement.

As shown in FIGS. 3(a) and 3(b), the rising degree of the current value of the exclusive standard solution as shown in FIG. 3(b) is significantly smaller than the rising degree of the current value at normal blood measurement as shown in FIG. 3(a) with the passage of time, because the oxidation current at exclusive standard solution measurement is suppressed by an effect of benzoic acid in the standard solution.

Therefore, the measuring device 14 detects the oxidation current value obtained from the third electrode 3 after a predetermined time has elapsed since the measurement sample is introduced into the sensor 13, and can automatically judge whether a type of sample solution is a standard solution sample or blood sample by comparing the detected oxidation current value to a predetermined threshold value.

Further, since a difference between the oxidation current values by which judgment of the types of sample solution is made significantly appears with the passage of time as shown in FIGS. 3(a) and 3(b), the oxidation current value obtained from the third electrode 3 immediately before making measurement of the current value corresponding to the glucose level by applying a voltage again is used for the judgment of the types of sample solution, thereby more accurately judging types of sample solution.

Next, the threshold value used for the judgment of the types of sample solution will be described.

Since the oxidation current value detected from the third electrode 3 varies in accordance with the affect of the concentration of glucose as a substrate, the threshold value is determined in view of the effect of the glucose density, thereby making more precise judgment.

Hereinafter, an illustrative example of a method for determining the threshold value in view of the effect of this glucose concentration will be described.

Blood samples having three types of the glucose concentrations, 50, 200, 600 (mg/dl), respectively, and a standard solution sample are prepared as measurement samples. Further, benzoic acid is combined with the standard solution at a weight ratio of 0.1%.

The threshold value is determined by applying a voltage of 0.5V to the third electrode 3 shown in FIG. 1 using the working electrode 1 as reference, then introducing these six types of samples into the sensor 13, thereafter measuring the oxidation current value obtained from the third electrode 3 for every 0.5 seconds, after once stopping the measurement at a point of time when a rise of the current value for the 0.5 seconds reaches 0.3 $\mu$A, and measuring and comparing the oxidation current values for each sample after one second has elapsed since this point of time. The measurement result of six types of samples according to the above-described measurement is indicated in table 1.

TABLE 1

| type of samples | glucose concentration (mg/dl) | oxidation current value ($\mu$A) |
|---|---|---|
| whole blood | 20 | 5 |
|  | 200 | 11 |
|  | 600 | 30 |
| standard solution | 20 | 0.4 |
|  | 200 | 0.9 |
|  | 600 | 2.4 |

That is, as shown in table 1, the oxidation current value of the standard solution is significantly small as compared with the oxidation current value of a whole blood sample. Therefore, when the glucose concentration is 20~600 (mg/dl), a discrimination can be performed between the blood sample and the standard solution sample by using the threshold value as described below.
1) in a case of oxidation current value $\geqq$ 3 $\mu$A, blood sample
2) in a case of oxidation current value<3 $\mu$A, standard solution In this way, the oxidation current value obtained from the third electrode 3 after a predetermined fixed time has elapsed is detected, and the detected oxidation current value is compared with the predetermined threshold value, thereby automatically judging whether the type of sample solution is the standard solution sample or the blood sample. Further, if the foregoing is previously programmed in the measuring device 14, when the current value corresponding to glucose level after applying the voltage again is displayed and stored, the whole blood sample and the standard solution sample can be full-automatically discriminated between to be displayed and stored.

Further, while the glucose sensor is taken as an example in this embodiment, the similar effect can be obtained as long as a measuring device for a simple type electrode biosensor, a sensor, and a standard solution are used for cholesterol, lactic acid or the like.

In addition, while one in which the judgment of the types of sample solution is made by comparing the oxidation current value obtained from the third electrode 3 to the predetermined threshold value is described in this embodiment, the judgment of the types of sample solution may be made on the basis of a difference between the time variations of the oxidation current values obtained from the third electrode 3.

Industrial Availability

The present invention provides a measuring apparatus which can automatically judge types of sample solution without artificial preoperation, a sensor used therefor, and an exclusive standard solution, comprises a third electrode besides a working electrode and a counter electrode, and judges types of sample solution by utilizing the fact that an oxidation current value obtained from the third electrode when the exclusive standard solution is a sample is significantly different from the oxidation current value obtained from the third electrode when blood is a sample.

What is claimed is:

1. A measuring apparatus for use with a biosensor having a reaction layer which reacts with a substance to be measured in a sample solution, on a working electrode, a counter electrode, and a third electrode which are provided on an insulating substrate, so as to bridge the respective electrodes, said measuring apparatus comprising:
   a measuring unit operable to measure contents of the substance to be measured from a current value which is produced by a reaction between the substance to be measured and the reaction layer, which reaction is obtained between the working electrode and the counter electrode, and to judge the type of the sample solution on the basis of an oxidation current value obtained between the third electrode and the counter electrode or between the third electrode and the working electrode.

2. The measuring apparatus using the biosensor of claim 1, wherein said measuring unit is operable to judge the type of the sample solution by comparing an oxidation current value obtained between the third electrode and the counter electrode or between the third electrode and the working electrode to a predetermined threshold value.

3. The measuring apparatus using the biosensor of claim 1, wherein said measuring unit is operable to judge the type of the sample solution on the basis of the time variations of the oxidation current value obtained between the third electrode and the counter electrode or between the third electrode and the working electrode.

4. The measuring apparatus of claim 1, wherein said measuring unit is operable to utilize a current value which is measured at the point of time when a time has further elapsed after the current value a predetermined current value, which current flows between the third electrode and the counter electrode or between the third electrode and the working electrode, as the oxidation current value which is used in performing the judgment of the type of the sample solution.

5. A measuring method using a biosensor having a reaction layer which reacts with a substance to be measured in a sample solution, on a working electrode, a counter electrode, and a third electrode which are provided on an insulating substrate, so as to bridge the respective electrodes, said method comprising:
   measuring contents of the substance to be measured from a current value which is produced by a reaction between the substance to be measured and the reaction layer, which reaction is obtained between the working electrode and the counter electrode, and judging the type of the sample solution on the basis of an oxidation current value obtained between the third electrode and the counter electrode or between the third electrode and the working electrode.

6. The measuring method of claim 5, wherein said judging comprises comparing an oxidation current value obtained between the third electrode and the counter electrode or between the third electrode and the working electrode, to a predetermined threshold value.

7. The measuring method of claim 5, wherein said judging comprises judging on the basis of time variations of the oxidation current value obtained between the third electrode and the counter electrode or between the third electrode and the working electrode.

8. The measuring method of claim 5, wherein the oxidation current value of said judging comprises a current value which is measured at the point of time when a prescribed time has further elapsed after the current value reached a predetermined current value, which current flows between the third electrode and the current electrode or between the third electrode and the working electrode.

9. The measuring method of claim 5, wherein the third electrode comprises materials which are more easily oxidized as compared with the materials of the working electrode and the counter electrode.

10. The measuring method of claim 5, wherein the third electrode comprises materials which have lower dissolution potentials than a voltage applied to the biosensor.

11. The measuring method of claim 5, wherein the third electrode comprises a material which is selected from the group consisting of silver, copper, zinc, and a mixed material including at least one of silver, copper, and zinc.

* * * * *